United States Patent [19]

Jakubowski et al.

[11] Patent Number: 5,604,236
[45] Date of Patent: Feb. 18, 1997

[54] BETA-CARBOLINE THROMBOXANE SYNTHASE INHIBITORS

[75] Inventors: Joseph A. Jakubowski, Indianapolis; Alan D. Palkowitz, Carmel, both of Ind.

[73] Assignee: Eli Lilly and Company, Indianapolis, Ind.

[21] Appl. No.: 436,052

[22] Filed: May 5, 1995

Related U.S. Application Data

[62] Division of Ser. No. 185,634, Jan. 24, 1994, abandoned.

[51] Int. Cl.$^6$ .......... C07D 471/04; A61K 31/44
[52] U.S. Cl. .......... 514/292; 546/85; 546/86; 546/87
[58] Field of Search .......... 546/85, 86, 87; 514/292

[56] References Cited

U.S. PATENT DOCUMENTS

| | | | |
|---|---|---|---|
| 2,850,501 | 9/1958 | Voegtli | 546/85 |
| 3,015,660 | 1/1962 | Robinson | 544/361 |
| 4,855,295 | 8/1989 | Biere et al. | 514/232.8 |
| 5,066,649 | 11/1991 | Hamminga et al. | 514/183 |

OTHER PUBLICATIONS

Chemical Abstracts, vol. 107, No. 1, 6 Jul. 1987, Columbus, Ohio, US; abstract no. 4667y.

Chemical Abstracts, vol. 197, No. 13, 27 Sep. 1982, Columbus, Ohio, US; abstract no. 110249y.

Chemical Abstracts, vol. 55, No. 19, 18 Sep. 1961, Columbus, Ohio, US; abstract no. 18788e.

Chemical Abstracts, vol. 58, No. 5, 4 Mar. 1963, Columbus, Ohio, US; abstract no. 4499e.

*Primary Examiner*—Alan L. Rotman
*Attorney, Agent, or Firm*—Roger S. Benjamin; David E. Boone

[57] ABSTRACT

Selected acid functional beta-carboline type derivatives effective as thromboxane synthase inhibitors having the formula:

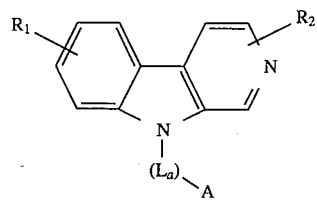

where $R_1$ and $R_2$ are monovalent radicals, —$(L_a)$— is a linking group of 4 to 8 chain atoms, and A is an acidic group.

2 Claims, No Drawings

BETA-CARBOLINE THROMBOXANE SYNTHASE INHIBITORS

This application is a division of application Ser. No. 08/185,634, filed Jan. 24, 1994, abandoned.

FIELD OF THE INVENTION

This invention concerns beta-carboline compounds useful as thromboxane synthase inhibitors.

BACKGROUND OF THE INVENTION

The tricyclic compound, beta-carboline (CA Registry No. 244-63-3), is also known as norharman; carbazoline; 2-azacarbazole; 2,9-diazafluorene; and 9H-pyrido(3,4-β)indole.

The preparation of certain esters of 9-pyrid(3,4-β)indole alkanoic acids is described in U.S. Pat. No. 2,850,501.

U.S. Pat. No. 5,066,649 describes various 8,9-annelated 1,2,3,4-tetrahydro-beta-carbolines as orally active fibrinolytics.

Therapeutic agents for specifically reducing the production of thromboxane $A_2$ are useful for treatment of conditions such as renal disease, (e.g., hydronephrosis, transplant rejection, and renal nephritis) pulmonary disease, (e.g., asthma, and pulmonary hypertension), prevention and treatment of hepatic and intestinal damage, cardiovascular diseases (e.g., arteriosclerosis, thrombosis, hypertension, and shock) or resulting from surgical procedures such as angioplasty and coronary bypass surgery. Aspirin has utility as a non-specific indirect inhibitor of thromboxane synthesis, however, it is desirable to discover new compounds having more potent and specific TSI properties than aspirin.

SUMMARY OF THE INVENTION

This invention is a novel series of beta-carboline type compounds which inactivate $TXA_2$ synthase in human blood platelets, said compounds having the general structural formula (I):

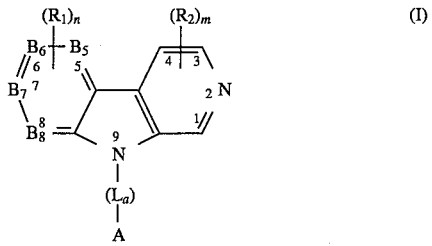

This invention is also a pharmaceutical formulation containing as active ingredient the beta-carboline compounds of formula (I); where $R_1$, $R_2$, n, m, $L_a$, A, $B_5$, $B_6$, $B_7$ and $B_8$ are as hereinafter defined.

This invention is also a multi-component pharmaceutical composition comprising the beta-carboline compound of the invention together with thrombolytic agents, angiotensin converting enzyme inhibitors, and/or thromboxane receptor antagonists.

This invention is a method of inhibiting thromboxane production by giving a mammal a therapeutically effective dose of a compound of the invention.

This invention is also an improved method of conducting surgical operations such as angioplasty and bypass surgery by administration to the patient a therapeutically effective dose of a compound of the invention.

DETAILED DESCRIPTION OF THE INVENTION

This invention relates to new thromboxane synthase inhibitors, and their use as antithrombotics for prophylaxis and treatment of thromboembolic diseases such as venous thrombosis, pulmonary embolism, arterial thrombosis, in particular myocardial ischemia, myocardial infarction and cerebral thrombosis, general hypercoagulable states and local hypercoagulable states such as following angioplasty and coronary bypass operations, and generalized tissue injury as it relates to the inflammatory process.

The following terms, have the definitions set out below:

The term "alkyl" by itself or as part on another substituent, unless otherwise stated means a straight or branched chain alkyl radical having the stated number of carbon atoms such as methyl, ethyl, n-propyl, isopropyl, n-butyl, and tertiary-butyl.

The term, "aryl" as used herein refers to an organic radical derived from an aromatic hydrocarbon by removal of one atom; e.g., phenyl, and naphthyl.

The term, "substituted phenyl" means a phenyl radical substituted at one or more positions by one or more $C_1$–$C_6$ alkyl, $C_1$–$C_6$ alkenyl, $C_1$–$C_6$ alkynyl, $C_1$–$C_6$ alkoxy, halo, nitro, sulfo, amino, or hydroxyl groups.

The term, "acidic group" refers to an organic radical which is a proton donor.

The term, "effective amount" as used herein, means an amount of the compound of the invention which is capable of inactivating $TXA_2$ synthase in human blood platelets to an extent which achieves a beneficial therapeutic and/or prophylactic result.

The words, "pharmacologically acceptable salts" include both acid and base addition salts.

The words, "chain atoms" means the number of atoms in the shortest chain between the two bonds of the linking group —($L_a$)—. The presence of a benzene or cyclohexane ring in the shortest chain counts as two atoms. For example, the linking groups (a) and (b);

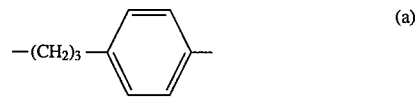

and

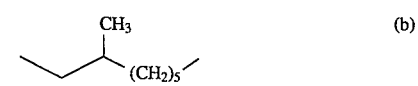

have 5 and 7 chain atoms, respectively.

I. Compounds of the Invention:

The novel compounds of the invention are represented by Formula (I) or a pharmacologically acceptable salt or prodrug thereof:

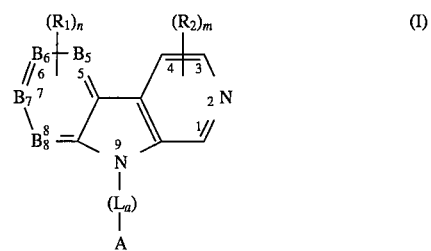

and wherein;

n is an integer from zero to 4;

m is an integer from zero to 3;

$B_5$, $B_6$, $B_7$, and $B_8$ are selected from the group consisting of carbon and nitrogen with the proviso that no more than two of $B_5$, $B_6$, $B_7$, or $B_8$ are nitrogen;

$R_1$ is a radical at position 5, 6, 7, or 8 where each $R_1$ is independently selected from hydroxy, halo, cyano, sulfo, nitro, amino, substituted amino, carboxyl, acyl, carbamyl, carbonyl, alkoxycarbonyl, aryl, aryloxy, $C_1$–$C_{12}$ alkyl, $C_1$–$C_{12}$ alkoxy, $C_4$–$C_8$ cycloalkyl, $C_1$–$C_{12}$ halogenated alkyl, $C_1$–$C_{12}$ hydroxylated alkyl, $C_1$–$C_{12}$ substituted phenyl, the phenyl of which may optionally be substituted by alkyl, halo, hydroxy, or alkoxy, $C_1$–$C_6$ alkenyl, $C_1$–$C_6$ alkynyl, $C_1$–$C_6$ alkylthio, acyl, $C_1$–$C_6$ alkoxy, or $C_1$–$C_6$ alkylsulfonyl;

$R_2$ is a radical at position 1, 3 or 4 where each $R_2$ is independently selected from hydroxy, halo, cyano, sulfo, nitro, amino, substituted amino, carboxyl, acyl, carbamyl, carbonyl, alkoxycarbonyl, aryl, aryloxy, $C_1$–$C_{12}$ alkyl, $C_1$–$C_{12}$ alkoxy, $C_4$–$C_8$ cycloalkyl, $C_1$–$C_{12}$ halogenated alkyl, $C_1$–$C_{12}$ hydroxylated alkyl, $C_1$–$C_{12}$ substituted phenyl, the phenyl of which may optionally be substituted by alkyl, halo, hydroxy, or alkoxy, $C_1$–$C_6$ alkenyl, $C_1$–$C_6$ alkynyl, $C_1$–$C_6$ alkylthio, acyl, $C_1$–$C_6$ alkoxy, or $C_1$–$C_6$ alkylsulfonyl;

positions 1, 3, 4, 5, 6, 7, and 8 in formula (I), where the ring atoms are carbon, not substituted by $R_1$ or $R_2$ are substituted with hydrogen;

($L_a$) is a divalent linking group; and

A is an acidic group.

Useful compounds of the invention are those wherein n is an integer from 1 to 4, and m is an integer from 1 to 3 and/or each $R_1$ and each $R_2$ is independently selected from the group consisting of; hydroxy, halogen, cyano, sulfo, nitro, amino, substituted amino, carboxyl, acyl, carbamyl, carbonyl, alkoxycarbonyl, aryl, aryloxy, $C_1$–$C_{12}$ alkyl, $C_1$–$C_{12}$ alkoxy, $C_4$–$C_8$ cycloalkyl, $C_1$–$C_{12}$ halogenated alkyl, $C_1$–$C_{12}$ hydroxylated alkyl, $C_1$–$C_{12}$ substituted phenyl, the phenyl of which may optionally be substituted by alkyl, halo, hydroxy, or alkoxy, $C_1$–$C_6$ alkenyl, $C_1$–$C_6$ alkynyl, $C_1$–$C_6$ alkylthio, acyl, $C_1$–$C_6$ alkoxy, or $C_1$–$C_6$ alkylsulfonyl.

Preferred are compounds of formula (I) wherein the acidic group A is selected from the following:

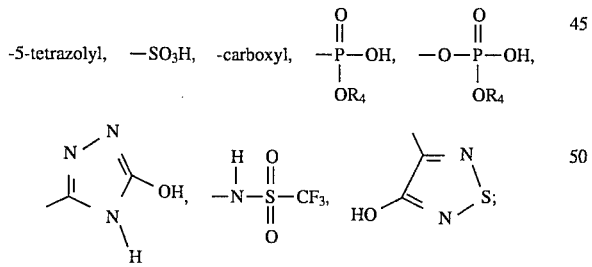

and where $R_4$ is selected from hydrogen, $C_1$–$C_{12}$ alkyl, phenyl or substituted phenyl.

Most preferred are compounds of formula (I) wherein the acidic group is carboxyl.

Also preferred are compounds of formula (I) wherein the divalent linking group —($L_a$)— has from 4 to 8 chain atoms and most preferably 5 or 6 chain atoms. Particularly preferred are compounds of Formula (I) wherein the divalent linking group, —($L_a$)—, is selected from the following formulae:

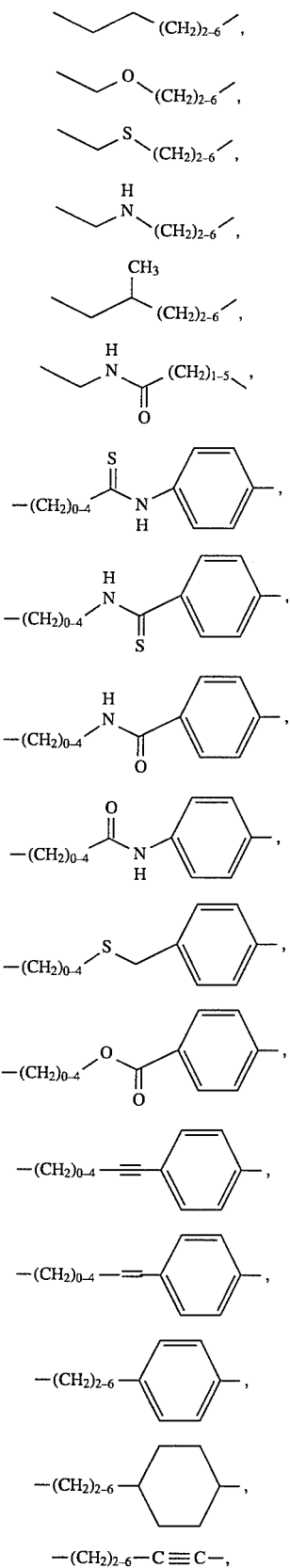

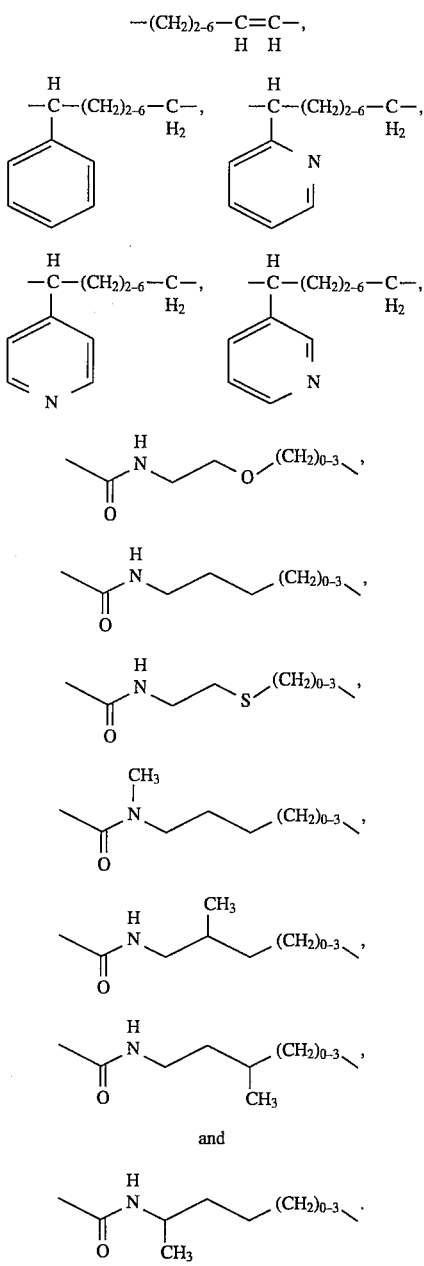

A preferred subset of Formula (I) beta-carboline compounds which inactivate TXA$_2$ synthase in human blood platelets is represented by Formula (II) and pharmacologically acceptable salts, solvates, or prodrugs thereof;

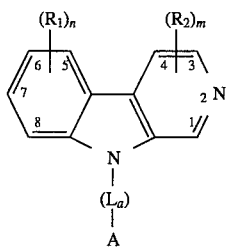
(II)

wherein;
n is an integer from zero to 4;
m is an integer from zero to 3;

R$_1$ is a radical at position 5, 6, 7, or 8 where each R$_1$ is independently selected from hydroxy, halo, cyano, sulfo, nitro, amino, substituted amino, carboxyl, acyl, carbamyl, carbonyl, alkoxycarbonyl, aryl, aryloxy, C$_1$–C$_{12}$ alkyl, C$_1$–C$_{12}$ alkoxy, C$_4$–C$_8$ cycloalkyl, C$_1$–C$_{12}$ halogenated alkyl, C$_1$–C$_{12}$ hydroxylated alkyl, C$_1$–C$_{12}$ substituted phenyl, the phenyl of which may optionally be substituted by alkyl, halo, hydroxy, or alkoxy, C$_1$–C$_6$ alkenyl, C$_1$–C$_6$ alkynyl, C$_1$–C$_6$ alkylthio, acyl, C$_1$–C$_6$ alkoxy, or C$_1$–C$_6$ alkylsulfonyl;

R$_2$ is a radical at position 1, 3 or 4 where each R$_2$ is independently selected from hydroxy, halo, cyano, sulfo, nitro, amino, substituted amino, carboxyl, acyl, carbamyl, carbonyl, alkoxycarbonyl, aryl, aryloxy, C$_1$–C$_{12}$ alkyl, C$_1$–C$_{12}$ alkoxy, C$_4$–C$_8$ cycloalkyl, C$_1$–C$_{12}$ halogenated alkyl, C$_1$–C$_{12}$ hydroxylated alkyl, C$_1$–C$_{12}$ substituted phenyl, the phenyl of which may optionally be substituted by alkyl, halo, hydroxy, or alkoxy, C$_1$–C$_6$ alkenyl, C$_1$–C$_6$ alkynyl, C$_1$–C$_6$ alkylthio, acyl, C$_1$–C$_6$ alkoxy, or C$_1$–C$_6$ alkylsulfonyl;

positions 1, 3, 4, 5, 6, 7, and 8 in formula (II) not substituted by R$_1$ or R$_2$ are substituted with hydrogen;

(L$_a$) is a divalent linking group containing from 4 to 6 chain atoms; and

A is an acidic group;

Useful compounds of Formula (II) are those wherein either n is zero (positions 5,6,7,8 are substituted with hydrogen), m is zero (positions 1,3,4 are substituted with hydrogen), or (n+m) are zero and A is carboxyl. Also preferred are compounds of Formula (II) wherein n is an integer from 1 to 4 and R$_1$ is selected from the group consisting of; hydroxy, halogen, cyano, sulfo, nitro, amino, substituted amino, carboxyl, acyl, carbamyl, carbonyl, alkoxycarbonyl, aryl, aryloxy, C$_1$–C$_{12}$ alkyl, C$_1$–C$_{12}$ alkoxy, C$_4$–C$_8$ cycloalkyl, C$_1$–C$_{12}$ halogenated alkyl, C$_1$–C$_{12}$ hydroxylated alkyl, C$_1$–C$_{12}$ substituted phenyl, the phenyl of which may optionally be substituted by alkyl, halo, hydroxy, or alkoxy, C$_1$–C$_6$ alkenyl, C$_1$–C$_6$ alkynyl, C$_1$–C$_6$ alkylthio, acyl, C$_1$–C$_6$ alkoxy, and C$_1$–C$_6$ alkylsulfonyl; and —(L$_a$)— is selected from the group consisting of;

—(CH$_2$)$_5$— and

—(CH$_2$)$_6$—;

and A is carboxyl.

A preferred subset of Formula (II) beta-carboline compounds which inactivate TXA$_2$ synthase in blood platelets and other cells is represented by Formula (III) and pharmacologically acceptable salts or prodrugs thereof.

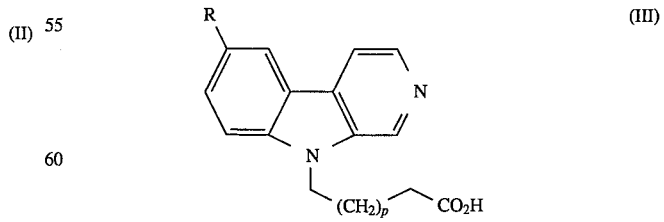
(III)

wherein;
p is an integer 3 or 4; and
R is hydrogen, hydroxy, halo, cyano, sulfo, nitro, amino, substituted amino, carboxyl, acyl, carbamyl, carbonyl, alkoxycarbonyl, aryl, aryloxy, C$_1$–C$_{12}$ alkyl, C$_1$–C$_{12}$ alkoxy, $C_4$–$C_8$ cycloalkyl, $C_1$–$C_{12}$ halogenated alkyl, $C_1$–$C_{12}$ hydroxylated alkyl, $C_1$–$C_{12}$ substituted phenyl, the phenyl of which may optionally be substituted by alkyl, halo, hydroxy, or alkoxy, $C_1$–$C_6$ alkenyl, $C_1$–$C_6$ alkynyl, $C_1$–$C_6$ alkylthio, acyl, $C_1$–$C_6$ alkoxy, or $C_1$–$C_6$ alkylsulfonyl;

or a pharmacologically acceptable salt, solvate, or prodrug thereof. A useful subset of compounds are those wherein R is not hydrogen.

Specific preferred compounds and all pharmaceutically acceptable salts, solvates and prodrug derivatives thereof which are illustrative of the compounds of the invention include the following:

(a) 9H-Pyrido (3,4-β)indole-9-butanoic acid,
(b) 9H-Pyrido (3,4-β)indole-9-pentanoic acid,
(c) 9H-Pyrido (3,4-β)indole-9-hexanoic acid,
(d) 6-Bromo-9H-pyrido(3,4-β)indole-9-hexanoic acid,
(e) 6-Nitro-9H-pyrido(3,4-β)indole-9-hexanoic acid,
(f) 6-Methyl-9H-pyrido(3,4-β)indole-9-hexanoic acid,
(g) 6-Methoxy-9H-pyrido(3,4-β)indole-9-hexanoic acid, and
(h) mixtures of any of (a) thru (g)

The compounds of the invention possess at least one acidic functional substituent (viz., group A of Formula I) and, as such, are capable of forming salts. Representative pharmaceutically acceptable salts, include but are not limited to, the alkali and alkaline earth salts such as lithium, sodium, potassium, calcium, magnesium, aluminum and the like. Salts are conveniently prepared from the free acid by treating the acid in solution with a base or by exposing the acid to an ion exchange resin.

Included within the definition of pharmaceutically acceptable salts are the relatively non-toxic, inorganic and organic base addition salts of compounds of the present invention, for example, ammonium, quaternary ammonium, and amine actions, derived from nitrogenous bases of sufficient basicity to form salts with the compounds of this invention (see, for example, S. M. Berge, et al., "Pharmaceutical Salts," *J. Phar. Sci.*, 66: 1–19 (1977)).

In those instances where the compounds of the invention contain a basic group(s) they may be reacted with suitable organic or inorganic acids to form salts such as acetate, benzenesulfonate, benzoate, bicarbonate, bisulfate, bitartrate, borate, bromide, camsylate, carbonate, chloride, clavulanate, cidrate, dihydrochloride, edetate, edisylate, estolate, esylate, fumarate, gluceptate, gluconate, glutamate, glycolylarsanilate, hexylresorcinate, hydrabamine, bromide, chloride, hydroxynaphthoate, iodide, isothionate, lactate, lactobionate, laurate, malate, malseate, mandelate, mesylate, methylbromide, methylnitrate, methylsulfate, mucate, napsylate, nitrate, oleate, oxalate, palmirate, pantothenate, phosphate, polygalacturonate, salicylate, stearate, subacetate, succinate, tannate, tartrate, tosylate, trifluoroacetate, trifluoromethane sulfonate, and valerate.

The compounds of the formula (I) can also be in the form of zwitterions, since they contain both acidic and basic functionality and are capable of self-protonation.

Certain compounds of the invention possess one or more chiral centers and may thus exist in optically active forms. Likewise, when the compounds contain an alkenyl or alkenylene group there exists the possibility of cis- and trans- isomeric forms of the compounds. The R- and S- isomers and mixtures thereof, including racemic mixtures as well as mixtures of cis- and trans- isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods.

Prodrugs are derivatives of the compounds of the invention which have chemically or metabolically cleavable groups and become by solvolysis or under physiological conditions the compounds of the invention which are pharmaceutically active in vivo. Derivatives of the compounds of this invention have activity in both their acid and base derivative forms, but the acid derivative form often offers advantages of solubility, tissue compatibility, or delayed release in a mammalian organism (see, Bundgard, H., Design of Prodrugs, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy) alkyl esters or ((alkoxycarbonyl)oxy)alkyl esters.

II. Pharmaceutical Formulations of the Invention:

This invention also provides pharmaceutical formulations comprising a novel compound as described in the preceding Section I or a pharmaceutically acceptable salt or prodrug thereof.

For the pharmaceutical formulations any suitable carrier known in the art can be used. In such a formulation, the carrier may be a solid, liquid, or mixture of a solid and a liquid. Solid form formulations include powders, tablets and capsules. A solid carrier can be one or more substances which may also act as flavoring agents, lubricants, solubilisers, suspending agents, binders, tablet disintegrating agents and encapsulating material.

In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from about 1 to about 99 weight percent of the active ingredient which is the novel compound of this invention. Suitable solid carriers are magnesium carbonate, magnesium stearate, talc, sugar lactose, pectin, dextrin, starch, gelatin, tragacanth, methyl cellulose, sodium carboxymethyl cellulose, low melting waxes, and cocoa butter.

Sterile liquid form formulations include suspensions, emulsions, syrups and elixirs.

The active ingredient can be dissolved or suspended in a pharmaceutically acceptable carrier, such as sterile water, sterile organic solvent or a mixture of both. The active ingredient can often be dissolved in a suitable organic solvent, for instance aqueous propylene glycol. Other compositions can be made by dispersing the finely divided active ingredient in aqueous starch or sodium carboxymethyl cellulose solution or in a suitable oil.

Preferably the pharmaceutical formulation is in unit dosage form. The unit dosage form can be a capsule or tablet itself, or the appropriate number of any of these. The quantity of active ingredient in a unit dose of composition may be varied or adjusted from about 0.1 to about 1000 milligrams or more according to the particular treatment involved. It may be appreciated that it may be necessary to make routine variations to the dosage depending on the age and condition of the patient. The dosage will also depend on the route of administration.

The formulations according to the invention may be made for oral, parenteral or rectal administration or in a form suitable for administration by inhalation or insufflation, either through the mouth or nose.

The following pharmaceutical formulations 1 thru 8 are illustrative only and are not intended to limit the scope of the invention in any way. "Active ingredient," refers to a compound according to Formula (I) or a pharmaceutically acceptable salt, solrate, or prodrug thereof.

Formulation 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2

A tablet is prepared using the ingredients below:

|  | Quantity (mg/capsule) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg

Formulation 3

An aerosol solution is prepared containing the following components:

|  | Weight |
| --- | --- |
| Active ingredient | 0.25 |
| Ethanol | 25.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| Active ingredient | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinyl-pyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| Active ingredient | 80 mg |
| --- | --- |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| Active ingredient | 225 mg |
| --- | --- |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| Active ingredient | 50 mg |
| --- | --- |
| Sodium carboxymethyl cellulose | 50 mg |
| Syrup | 1.25 ml |

-continued

| Benzoic acid solution | 0.10 ml |
|---|---|
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| Active ingredient | 100 mg |
|---|---|
| Isotonic saline | 1,000 ml |

The solution of the above ingredients generally is administered intravenously to a subject at a rate of 1 ml per minute. The pharmaceutical formulations of the invention inactivate $TXA_2$ synthase in human blood platelets.

III. Multi-Mode Pharmaceutical Formulations Using Compounds of the Invention in Combination with Selected Therapeutic Agents:

The compounds of the invention act as thromboxane synthase inhibitors and are advantageously combined with other agents having different modes of action to give multi-mode pharmaceutical compositions. The resultant combination of ingredients may be used as Active Ingredient in the pharmaceutical formulations described in Section II, above. Thus, an Active Ingredient (for multi-mode pharmaceutical formulations) may be formed by combining the compounds of this invention (as represented by Formulae I, II, and III) with therapeutic agents selected from one or more of the following classes:

a) thrombolytic agents;
b) angiotensin converting enzyme inhibitors;
c) thromboxane receptor antagonists.

Examples of thrombolytic agents (a) are tissue plasminogen activator (t-PA) and streptokinase. These agents would be preferably used in combination with the compounds of the invention for cardiovascular indications.

Examples of angiotensin converting enzyme inhibitors (b) are ACE inhibitors (e.g., captopril, 1-[(2S)-3-mercapto-2-methylpropionyl]-L-proline). These inhibitors would be preferably used in combination with the compounds of the invention for renal indications such as diabetic nephropathy.

Examples of thromboxane receptor antagonists (c) are Vapiprost (Glaxo) and S-1452™ compound (CAS Reg. No.132747-47-8); (5-Heptanoic acid, 7-[3-[(phenylsulfonyl) amino]bicyclo[2.2.1]hept-2-yl]-calcium salt (2:1), [1R-[1α, 2α(Z),3β, 4α]]; and VAPIPROST™ compound (CAS Reg. No. 87248-13-3); [1R-[1α(Z),2β,3β,5α]]-(+)-7-[5-[(1, 1'-Biphenyl)-4-ylmethoxy]-3-hydroxy-2-(1-piperidinyl)cyclopentyl]-4-heptenoic acid hydrochloride; and Bay-u-3405™ compound (CAS Reg. No.116649-85-5); (9H-Carbazole-9-propanoic acid, 3-[[(4-fluorophenyl)sulfonyl] amino]-1,2,3,4-tetrahydro, (R)-. These antagonists would preferably be used in combination with the compounds of the invention for cardiovascular and renal indications. Combinations of the compounds of the invention with thromboxane receptor antagonist (TRA) is a preferred aspect of this invention, because the (TRA) blocks the activity of prostaglandin $H_2$ which is enhanced by the thromboxane synthase inhibitor compounds of the invention (represented by formulae I, II, and III).

The relative proportions of ingredients (weight ratio of compounds of the invention to therapeutic agent) will generally be in the range of from 1 to 1000 to 1000 to 1 and is readily determined by combining dosages of the ingredients in weights known to be pharmaceutically effective.

Multi-mode pharmaceutical composition may be formed by admixing the compounds of the invention with one or more classes of therapeutic agent (a), (b), or (c) listed above. Alternatively, each ingredient, (i) the compound of the invention, and (ii) the selected therapeutic agent may be packaged together, for example in a tablet having two parts, so their administration to the patient is concurrent.

IV. An Improved Method of Inhibiting Thromboxane Production Using Compounds of the Invention:

This invention is a method for inhibiting thromboxane production which comprises administering to a mammalian host (e.g. human) an effective amount of the novel compounds for formulae (I), (II), or (III). The treatment of a mammal with the compounds of the invention may be for either therapeutic and/or prophylactic purposes.

A preferred method of the invention for inhibiting thromboxane production is administration to a mammal of the pharmaceutical formulations of the invention described in Section II, above, or the multi-mode pharmaceutical formulations described in Section III, above.

A specific dose of a compound of the invention administered to obtain therapeutic and/or prophylactic effects will, of course, be determined by the particular circumstances surrounding the case, including, for example, the route of administration and the condition being treated. A typical daily dose will contain a non-toxic dosage level of compound of from about 0.01 mg/kg to about 50 mg/kg of body weight. Preferred daily doses generally will be from about 0.05 mg/kg to about 20 mg/kg.

This invention is also an improved method of conducting angioplasty by administering before and/or during the angioplasty the thrombosis preventing novel compounds of formulae (I), (II) or (III).

This invention is a method for the prevention or treatment of a first or recurrent myocardial infarction or a first or recurrent stroke in a human comprising administering to the human in an amount effective for prevention or treatment of a first or recurrent myocardial infarction for first or recurrent stroke, a combination of active ingredients comprising the compounds of formulae (I), (II) or (III) or a pharmaceutically acceptable salt or prodrug thereof.

V. Method of Preparing the Beta-Carboline Compounds of the Invention:

Method A:

One method of preparing the compounds of the invention is described in U.S. Pat. No. 2,850,501; the disclosure of which in incorporated herein by reference. Thus, in the U.S. Pat. No. 2,850,501 disclosure for preparation of 9-pyrid(3, 4-β)indole alkanoic acids an alkali metal derivative of beta-carboline is reacted with a suitable ester of a haloalkanol, and the condensation product then reacted with an alkali metal cyanade. For example, a lithium derivative of beta-carboline is first prepared by reacting beta-carboline with phenyllithium, followed by reaction with 3-chloropropyl-p-toluene sulfonate. The resulting 9-pyrid(3,4-β)indolepropyl chloride may then be reacted with potassium cyanide to yield 9-pyrid(3,4-β)indolebutyronitrile from which alkyl carboxylic acid esters can be prepared directly by acid hydrolysis of the nitrile in a solvent comprising acid or the proper alcohol.

Method B:

Alternatively, beta-carboline compounds containing an —$(L_a)$—COOH pendent group at the 9 position may be conveniently produced by deprotonating a beta-carboline starting material (1) with base to give product (2), which is then reacted with a halo-alkanoate to give an ester derivative (3), which is thereafter hydrolyzed with base to give an acid derivative (4) as shown in reaction scheme below:

Scheme (Method B)

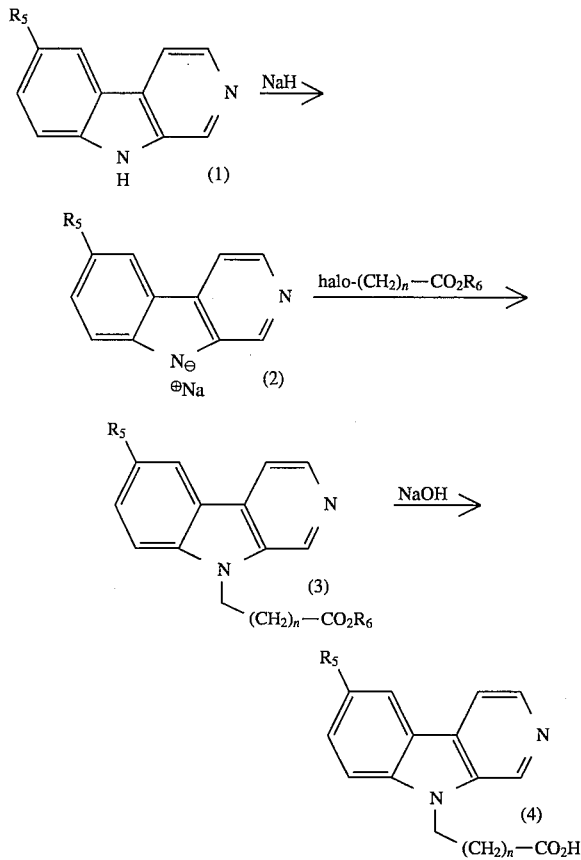

The following Examples are intended to illustrate the invention and are not to be construed as being limitations thereon. Temperatures are given in degrees Centigrade and all parts wherever given are parts by weight unless otherwise indicated.

EXAMPLES

Example 1

Preparation of 9H-Pyrido(3,4-β)indole-9-hexanoic acid, a compound of this invention represented by the formula (IV):

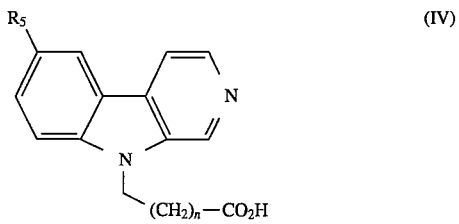

where n=4, $R_5$=H

To a slurry of NaH (0.75 g, 18.7 mmol, 60% dispersion in mineral oil) in 15 mL of anhydrous DMF at room temperature was added 9H-pyrido(3,4-β)indole (2.62 g, 15.6 mmol) in small portions. When gas evolution ceased, halo-alkanoate (ethyl-6-iodohexanoate, 5.30 g, 19.5 mmol) was introduced dropwise via syringe. The resulting mixture was stirred at room temperature for 5 hours. The reaction was quenched by pouring the solution into cold $H_2O$ (100 mL). The aqueous was extracted with EtOAc (3×100 mL). The organic was dried ($Na_2SO4$) and concentrated in vacuo to an oil. Chromatography (70/30 EtOAc/hexanes, $SiO_2$) provided 3.30 g (68%) of ethyl-9H-pyrido(3,4-β)indole-9-hexanoate as an amber oil. Analysis. Calcd. for $C_{19}H_{22}N_2O_2$: C, 73.52; H, 7.14; N, 9.02. Found: C, 73.22; H, 7.33; N, 8.99.

Ethyl-9H-pyrido(3,4-β)indole-9-hexanoate (2.0 g, 6.45 mmol) was dissolved in a mixture of THF (2.0 mL) and 2N NaOH (5.0 mL). The resulting mixture was stirred at room temperature for 18 hours. The pH of the reaction was adjusted to 2.0 using 1N HCl. The aqueous was extracted with EtOAc (2×10 mL). 9H-Pyrido(3,4-β)indole-9-hexanoic acid precipitated from the EtOAc solution as a white solid and was collected by filtration. An additional amount of product was recovered by adjusting the pH of the aqueous to 3.5 using 1N NaOH. The product precipitated and was collected by filtration. Total recovery of 9H-pyrido(3,4-β)indole-9-hexanoic acid was 1.38 g (75%). Haloalkanoate preparation details are set out in Table 1.

Example 2

The compound of Example 2 represented by formula (IV) is outside the scope of the invention (value of n too small) and is prepared using the general method of Example 1. Properties and preparation details are set out in Table 1.

Examples 3 to 8

The compounds of Examples 3, 4, 5, 6, 7, and 8 defined by formula (IV) are within the scope of the invention and are prepared using the general method of Example 1. Properties and preparation details are set out in Table 1 below:

TABLE 1

| | formula (IV) | | | |
|---|---|---|---|---|
| Example | $R_5$ | n | m.p. | note |
| 1 | H | 4 | 161–164 | 1 |
| 2 | H | 2 | 226–229 | 2 |
| 3 | H | 3 | 162–165 | 3 |
| 4 | H | 5 | 156–158 | 4 |
| 5 | Br | 4 | 177–179 | 5 |
| 6 | $CH_3$ | 4 | 167–169 | 6 |
| 7 | $CH_3O$ | 4 | 165–167 | 7 |
| 8 | $NO_2$ | 4 | 222–224 | 8 | note 1—Ethyl-6-iodohexanoate is prepared by the method dislosed in in *Synthesis* 1982, p.963, the disclosure of which is incorporated herein by reference. Yield 51%

Calculated: $C_{17}H_{18}N_2O_2$: C, 72.32; H, 6.43; N, 9.92 Found: C, 72.23; H, 6.49; N, 9.95 note 2—Ethyl-4-bromobutanoate is used in place of ethyl-6-iodohexanoate in the method of Example 1. Yield 20%.

Calculated: $C_{15}H_{14}N_2O_2$: C, 70.85; H, 5.55; N, 11.02 Found: C, 71.13; H, 5.61; N, 11.23.

note 3—Ethyl-5-bromovalerate is used in place of ethyl-6iodohexanoate in the method of Example 1. Yield 26%.

Calculated: $C_{16}H_{16}N_2O_2$: C, 71.62; H, 6.01; N, 10.44 Found: C, 71.90; H, 6.08; N, 10.50.

note 4—Ethyl-7-bromoheptanoate is used in place of ethyl-6-iodohexanoate in the method of Example 1. Yield 33%.

Calculated: $C_{18}H_{20}N_2O_2$: C, 72.95; H, 6.80; N, 9.45
Found: C, 72.72; H, 6.91; N, 9.65.

note 5—Starting material (bromine β-carboline derivative) is prepared by the method disclosed in J. Am. Chem. Soc. 1987, 109, pages 3378–3387, see, p. 3378 compound 14; the disclosure of which is incorporated herein by reference. Ethyl-6-iodohexanoate used as Example 1. Yield 21%

Calculated: $C_{17}H_{17}BrN_2O_2$: C, 56.52; H, 4.74; N, 7.76
Found: C, 56.55; H, 4.72; N, 7.51.

note 6—Starting material (methyl β-carboline derivative) is prepared using 6-methyl tryptamine in the method disclosed in Org. Syn. Coll. Vol. VI, P. 965, J. Chem. Soc. 1952, p. 650 and J. Chem. Soc. 1946, p. 617; the disclosure of which is incorporated herein by reference. Ethyl-6-iodohexanoate is used as Example 1. Yield 26%.

Calculated: $C_{18}H_{20}N_2O_2$: C, 72.94; H, 6.80; N, 9.45
Found: C, 72.67; H, 6.88; N, 9.15.

note 7—Starting material (methoxy β-carboline derivative) is prepared using 6-methoxy tryptamine in the method disclosed in Org. Syn. Coll. Vol. VI, P. 965, J. Chem. Soc. 1952, p.650 and J. Chem. Soc. 1946, p.617; the disclosure of which is incorporated herein by reference. Ethyl-6-iodohexanoate is used as Example 1. Yield 25%.

Calculated: $C_{18}H_{20}N_2O_3$: C, 69.21; H, 6.45; N, 8.97
Found: C, 68.94; H, 6.49; N, 8.81.

note 8—Starting material (nitro β-carboline derivative) is prepared as described in Heterocycles 1983, 20, p.1295, 1303, the disclosure of which is incorporated herein by reference. Ethyl-6-iodohexanoate is used as Example 1. yield 19%

Calculated: $C_{17}H_{17}N_3O_4$: C, 62.38; H, 5.23; N, 12.84
Found: C, 62.24; H, 5.38; N, 12.56.

ASSAY

The ability of the compounds of the present invention to be an effective thromboxane synthase inhibitors were evaluated in the following Thromboxane Synthase Inhibition (TSI) Assay with the results shown in Table 2 below:

TABLE 2

| Compound of Example No. | IC$_{50}$ (nM) |
| --- | --- |
| 1 | 53 |
| 2 | 19,000 |
| 3 | 100 |
| 4 | 210 |
| 5 | 68 |
| 6 | 31 |
| 7 | 49 |
| 8 | 91 |

Method for Thromboxane Synthase Inhibition (TSI) Test

The test compounds were dissolved in dimethylsulfoxide. The compound solutions were incubated with fresh whole human blood, that had been anticoagulated with 0.38% trisodium citrate, for 30 minutes at 37° C. After 30 minutes, 0.025 ml of 0.5M calcium chloride solution was added to each 1 ml of blood and further incubated for one hour at 37° C. Serum was prepared by centrifugation of the blood at 2000×g for 15 minutes in a Beckman table top centrifuge. Serum TXB$_2$ and 6-keto-PGF$_{1\alpha}$, the stable metabolites of TXA$_2$ and markers of synthesis of TXA$_2$ and prostacyclin respectively, were measured by radioimmunoassay by commonly used test methods (see, Refs.,1 & 2 below). Results from the radioimmunoassay of TXB$_2$ were used to calculate the IC$_{50}$ (concentration of compound required to reduce thromboxane generation to 50% of that obtained with vehicle alone).

Data determined from the radioimmunoassay of 6-keto-PGF$_{1\alpha}$ (reflecting prostacyclin generation) allowed a determination of the specificity of the compound of example 1 for the inhibition of thromboxane synthase as indicated by increased levels of 6-keto-PGF$_{1\alpha}$ relative to the less specific inhibition of cyclooxygenase by aspirin. Aspirin is well known to completely inhibit the generation of 6-keto-PGF$_{1\alpha}$. The data in Table 3 documents the expected dose-dependent stimulatory effect of the compound of example 1 on human serum 6-keto-PGF$_{1\alpha}$ levels.

TABLE 3

| Compound of Example 1 concentration (μM) | Serum 6-keto-PGF$_{1a}$ (ng/ml) |
| --- | --- |
| 0 (vehicle) | 2.43 |
| 0.001 | 3.01 |
| 0.01 | 5.09 |
| 0.1 | 7.07 |
| 1 | 7.71 |
| 10 | 7.82 |

The oral activity of the compound of example 1 was established by treating rats via the oral route with solutions of the compound and one hour later blood was collected. The blood was allowed to clot in glass tubes for 1 hour at 37° C. Serum was collected after sedimentation of the clot by centrifugation at 2000×g for 15 minutes in a Beckman table top centrifuge. The levels of TXB$_2$ were measured in the serum by radioimmunoassay. Decreased levels of TXB$_2$ indicate the presence of compound in the blood resulting from oral absorption. Similar experiments were performed following introduction of the compound directly into the blood by bolus intravenous (i.v.) infusions of solutions of the compound of example 1 with blood collection and serum preparation 15 minutes later. The results of these experiments are shown in Table 4 and document the availability of the compounds by both oral and i.v. routes.

TABLE 4

| Administered dose mg/kg | Serum TXB$_2$ (% control) i.v. administration | Serum TXB$_2$ (% control) oral administration |
| --- | --- | --- |
| 0 (vehicle) | 100 | 100 |
| 0.01 | 69 | n.t. |
| 0.1 | 14 | 54 |
| 1 | 4 | 16 |
| 10 | n.t. | 2 |
| 100 | n.t. | 1 | n.t. = not tested

Ref. 1. Sors, H., Pradelles, P and Dray, F. *Prostaglandins*, 16:277, 1978

Ref. 2. Dray, et al. *Advances in Prostaglandin and Thromboxane Research* 6:167, 1980.

What is claimed is:

1. A beta-carboline compound which inactivates TXA$_2$ synthase in mammalian blood platelets, said compound or a pharmacologically acceptable salt, solvate, or prodrug thereof represented by the formula (III):

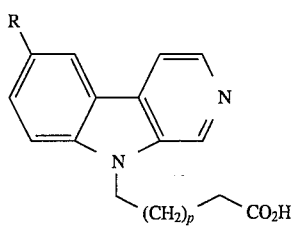

wherein;

R is a radical selected from halo, $C_1$–$C_{12}$ alkyl, $C_1$–$C_{12}$ alkoxy, nitro, cyano; and p is an integer 3 or 4.

2. A method of inactivating $TXA_2$ synthase in mammalian blood platelets by administering an effective amount of a beta-carboline compound or a pharmacologically acceptable salt, solvate, or prodrug thereof represented by the formula (III):

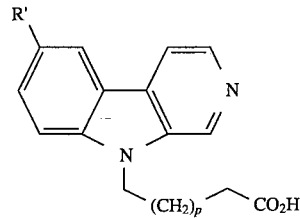

wherein;

R' is a radical selected from hydrogen, halo, $C_1$–$C_{12}$ alkyl, $C_1$–$C_{12}$ alkoxy, nitro, cyano; and p is an integer 3 or 4.

* * * * *